(12) United States Patent
Markoski

(10) Patent No.: US 6,264,893 B1
(45) Date of Patent: Jul. 24, 2001

(54) METHOD AND APPARATUS FOR DEVELOPING THIN LAYER CHROMATOGRAPHY PLATES FOR MAXIMIZING MOBILE PHASE CONDITIONS IN COLUMN CHROMATOGRAPHY

(76) Inventor: Larry J. Markoski, 303 W. Green St. #D202, Champaign, IL (US) 61820

( * ) Notice: Subject to any disclaimer, the term of this patent is extended or adjusted under 35 U.S.C. 154(b) by 0 days.

(21) Appl. No.: 09/290,215

(22) Filed: Apr. 13, 1999

Related U.S. Application Data

(60) Provisional application No. 60/081,457, filed on Apr. 13, 1998.

(51) Int. Cl.[7] .................................................. G01N 30/90
(52) U.S. Cl. ..................... 422/70; 73/61.54; 210/198.3; 422/102; 422/104; 436/162
(58) Field of Search ............................. 422/70, 102, 104; 436/162; 210/198.3; 73/61.54

(56) References Cited

U.S. PATENT DOCUMENTS

| | | |
|---|---|---|
| 2,986,280 | 5/1961 | Magnuson et al. . |
| 3,265,214 | 8/1966 | Brodsky . |
| 3,341,017 * | 9/1967 | Powell . |
| 3,474,031 * | 10/1969 | Blondeel . |
| 3,667,917 | 6/1972 | Brandt . |
| 3,752,316 | 8/1973 | Takeshita . |
| 3,904,372 * | 9/1975 | Lightner . |
| 3,928,203 | 12/1975 | Kremer . |
| 4,469,660 | 9/1984 | Jones et al. . |

OTHER PUBLICATIONS

Still et al., "Rapid Chromatographic Technique for Preparative Separations with Moderate Resolution" J. Org. Chem. 43 :2923–2925 (1970).

Pavia et al., Organic Laboratory Techniques, A Microscale Approach, Saunders College Publishing, Philadelphia, Chapters 12–13, pp. 696–737 (1990).

* cited by examiner

Primary Examiner—Jan Ludlow
(74) Attorney, Agent, or Firm—Roberts & Mercanti, L.L.P.

(57) ABSTRACT

An apparatus for conducting multiple thin layer chromatographic processes including an array of receptacles, each receivable of chromatographic fluid, a support structure for supporting the receptacles, and a retaining unit for retaining thin layer chromatographic plates while enabling each plate to be inserted into and removed from a respective receptacle. In use, one or more samples of interest are spotted onto multiple thin layer chromatography plates, the chromatography receptacles are filled with a suitable amount of a chromatography solvent, the plates are inserted into respective chambers to begin the chromatography process and the processes are allowed to continue for a sufficient time period for sample separation to occur. Any separated samples are readily visualized and detected.

28 Claims, 7 Drawing Sheets

METHOD AND APPARATUS FOR DEVELOPING THIN LAYER CHROMATOGRAPHY PLATES FOR MAXIMIZING MOBILE PHASE CONDITIONS IN COLUMN CHROMATOGRAPHY

This application claim benefit to provisional application No. 60/081,457 Apr. 13, 1998.

FIELD OF THE INVENTION

This invention relates to an apparatus and method for performing multiple, simultaneous, thin-layer chromatography chemical tests. The apparatus consists of a holder for a matrix of developing chambers for assaying the chemical purity of materials utilizing thin-layer chromatography.

BACKGROUND OF THE INVENTION

The invention relates to an apparatus and method for improving the speed and efficiency in performing thin layer chromatography (TLC) tests. Thin layer chromatography, one of the most standard laboratory techniques, is a solid-liquid partitioning technique used in chemical analysis. It is a micro-scale technique since only micrograms of material are needed to perform the analysis. A thin layer chromatography plate consists of a thin layer of adsorbent material (stationary phase) coated on a backing support. Typically, the support is, but is not limited to, a glass plate and the adsorbent material is, but is not limited to, a silica/silicate material. When the thin layer plate is partially submerged in a liquid (mobile phase), the liquid ascends the adsorbent by capillary action. By placing a small spot of a solution containing two compounds near the base of the thin layer plate, yet not immersed in the solvent, the ascending liquid carries the sample and partitions the sample between the adsorbent stationary phase and the liquid mobile phase (commonly referred to as developing). After development, the plate can be visualized and the distance a given compound travels with respect to the distance the solvent travels is referred to as the compounds Rf value and is expressed as a ratio. The Rf value is determined by a number of factors, namely the chemical structure of the compound and its interactions with the prescribed stationary and mobile phases. Changing the composition of either the stationary phase compound or mobile phase solvent can have dramatic effects on not only how far the sample travels with respect to the solvent front (Rf), but how tightly the compound travels together (the spot size and shape).

Different compounds have different interactions with the prescribed mobile and stationary phases and have a unique Rf of their own. Hence, thin layer chromatography is useful in determining the number of compounds in a given mixture. If the compounds in the mixture have very different chemical structures and the mobile/stationary phases are chosen properly, upon elution (development) the compounds will separate into their own spots with visible Rf differences between the spots. However, if the compounds have very similar chemical structure and/or the mobile/stationary phases are chosen poorly, the compounds may barely separate, if at all.

When ascertaining the chemical purity of a sample by TLC, the spot shape or the Rf difference between spots is not that crucial as long as all of the components of the mixture can be visualized. However, when one wants to physically separate the components of the mixture, the spot shape and the Rf difference between spots are crucial criteria when transferring what has been learned by TLC to the more macro-scale (mg-Kg) separation technique of column chromatography.

Column chromatography consists of a column, usually glass, a mobile phase, and a solid phase just as in thin layer chromatography. The adsorbent is packed into the column and the sample is loaded on top of the adsorbent. The mobile phase is then applied to the top of the column and flows through the column by either gravity or slight positive pressure. As in TLC, the column chromatography sample is partitioned between the mobile and stationary phases and depending upon the chemical structure of the compound, and the consistency of the mobile and stationary phases, the compound traverses down the column in a band. When a mixture of compounds is applied to the top of the column, and the proper mobile and stationary phases are chosen, as the solvent flows through the column the compounds separate into bands which can be isolated into pure compounds by collecting the bands as they elute out of the bottom of the column, commonly referred to as collecting fractions. When the consistency of these fractions is to be ascertained, one puts a spot from each fraction on a TLC plate and elutes (develops) with the same mobile and stationary phases as were run in the column. The factors that contribute to how well the compounds separate, are the volume of the fractions taken, the (low rate of the mobile phase, and most dramatically, the distance between the edges of the bands which is determined by the consistency of the mobile stationary phases. When the distance (between band edges) is large or when the bands are narrow, good separation can be achieved. Fractions 1–3 (figure not shown) can be combined and contain only pure compound A, fractions 4–7 (figure not shown) can be combined and contain only pure compound B, fractions 8–9 (figure not shown) can be combined and contain only pure compound C, and fractions 10–11 (figure not shown) can be combined and contain only pure compound D (Once compounds are pure, their structure can be elucidated by other spectroscopic means). However, when the distance (between band edges) is small or when the bandwidths are large, there can be a good amount of overlap in the fractions, such that only a few fractions contain pure compound. The other fractions either have to be thrown out, or resubmitted to another column chromatographic separation, which makes structure elucidation cumbersome if not impossible. This outcome is very undesirable from a synthetic standpoint, because it results in a loss of chemical yield and purity, and also a large loss of time if the mixtures have to be resubmitted to another column chromatographic separation. In all, poor separation is a very costly outcome.

The secret to separating mixtures of compounds using column chromatography rests in the ability to maximize the distance between bands and also minimize the width of the bands. The two greatest factors that influence this separation arc the consistency of the mobile and stationary phases. Since the typical number of stationary phases is limited to typically three or four substances, the chemist has at his disposal many pure mobile phases and an unlimited number of solvent combinations. However, one skilled in the art learns to get a feel of how to limit this number through trial and error and also prior experience. By testing a small number of solvents or combinations on TLC plates, using trial and error and experience, one can invest a tremendous amount of time trying to find an adequate mobile phase, since this is usually done in a linear stepwise non-scientific manner. This method often works, but this limited exploration and personal bias often lead to a solvent system that gives non-optimal separation between spots or large spot diameters, which when transferred to a column chromatographic separation often results in band overlap which reduces chemical purity and yield. This old method, as previously stated, is extremely undesirable especially if the compound being purified is extremely expensive and any loss of yield or purity is a loss of money.

OBJECTS OF THE INVENTION

It is therefore an object of the present invention to provide an apparatus and method for performing thin-layer chromatography testing that allows multiple tests to be conducted simultaneously, using a grid of varying solvents and varying concentrations.

It is another object of the present invention to allow chromatography testing of an unknown material using less of the material. Preliminary identification of the material using thin-layer chromatography will save time and money before proceeding to column chromatography testing.

SUMMARY OF THE INVENTION

Accordingly, the invention consists of an apparatus and method for using same, that optimizes mobile phase conditions for a given stationary phase TLC plate (smallest spot sizes, greatest Rf differences between spots, and greatest solubility). When the optimized conditions are translated to column chromatography, all other variables being considered equal (flow rate, amount of stationary phase, and fraction size), this will lead to the narrowest bands and/or greatest distance between bands that can be achieved with the prescribed stationary phase, hence the best separation that can be achieved. The apparatus consists of an n×n array of TLC developing chambers, typically test tubes, and a method of running multiple simultaneous TLC plates with multiple mobile phases. The chambers are arranged in a grid of rows and columns to supply the greatest organization. The preferred embodiment for the apparatus is a 10 column×10 row grid of developing chambers. This is preferred because of the ability to vary the concentrations in increments of 10 percent.

Thus, the invention provides apparatus for conducting multiple, preferably simultaneous, thin layer chromatographic processes, including an array of multiple thin layer chromatography chambers, the array being held by one or more supports and each chromatography chamber comprising a thin layer chromatography plate. The array can optionally include n×n chromatography chambers, wherein n is an integer ranging from 5 to 10. Although in the following description the term "chamber" will be used, it should be understood by those skilled in the art that this term encompasses any means defining a space or cavity capable of receiving a solvent, such as a container, a vessel or a receptacle.

Each thin layer chromatography chamber is held in a fixed array by a top and bottom support. For example, each thin layer chromatography chamber is positioned in a receiving indentation in a supporting base and is held in place by an upper plate.

The invention also provides methods for conducting multiple liquid chromatographic assays using the provided apparatus. The chromatographic assays can be performed substantially simultaneously if so desired. Broadly, the method includes the steps of (a) spotting one or more samples of interest onto each of the multiple thin layer chromatography plates, (b) filling multiple thin layer chromatography chambers with a suitable amount of a chromatography solvent, (c) starting the chromatography processes for the thin layer chromatography plates simultaneously, and allowing the processes to continue for a sufficient time period for sample separation to occur, and (d) visualizing or detecting the separated samples.

Reference Numerals in the Drawings

Figure 1:
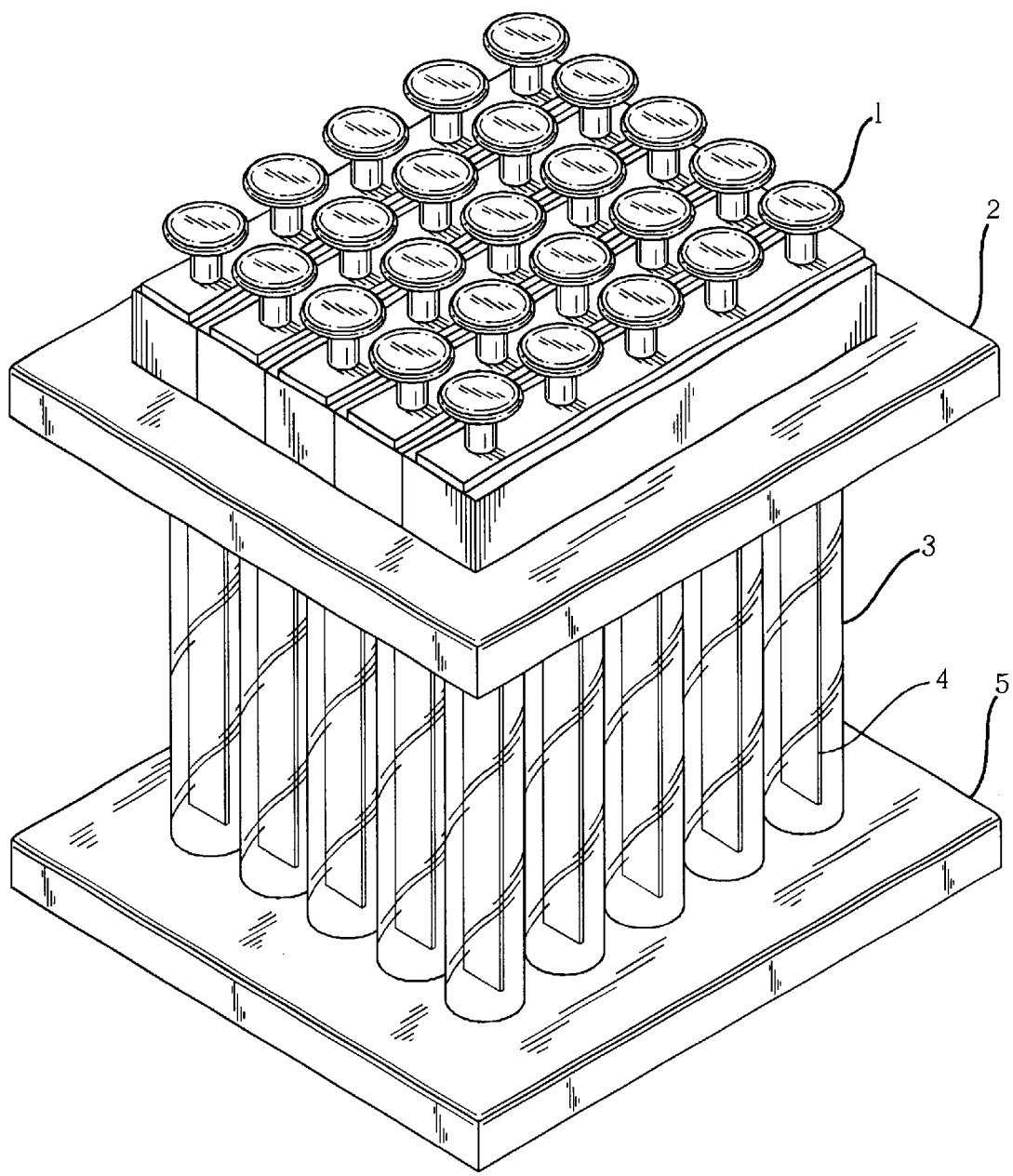
FIG. 1 is a perspective of a five-by-five grid of the invention.

1. Plunger
2. Top plate
3. Test tube
4. Thin layer chromatography plate
5. Base plate
6. Mounting plate
7. Plunger block
8. Plate holding clip (not shown)
9. Plate holding frame
10. Support

DETAILED DESCRIPTION OF THE PREFERRED EMBODIMENT

Figure 3:
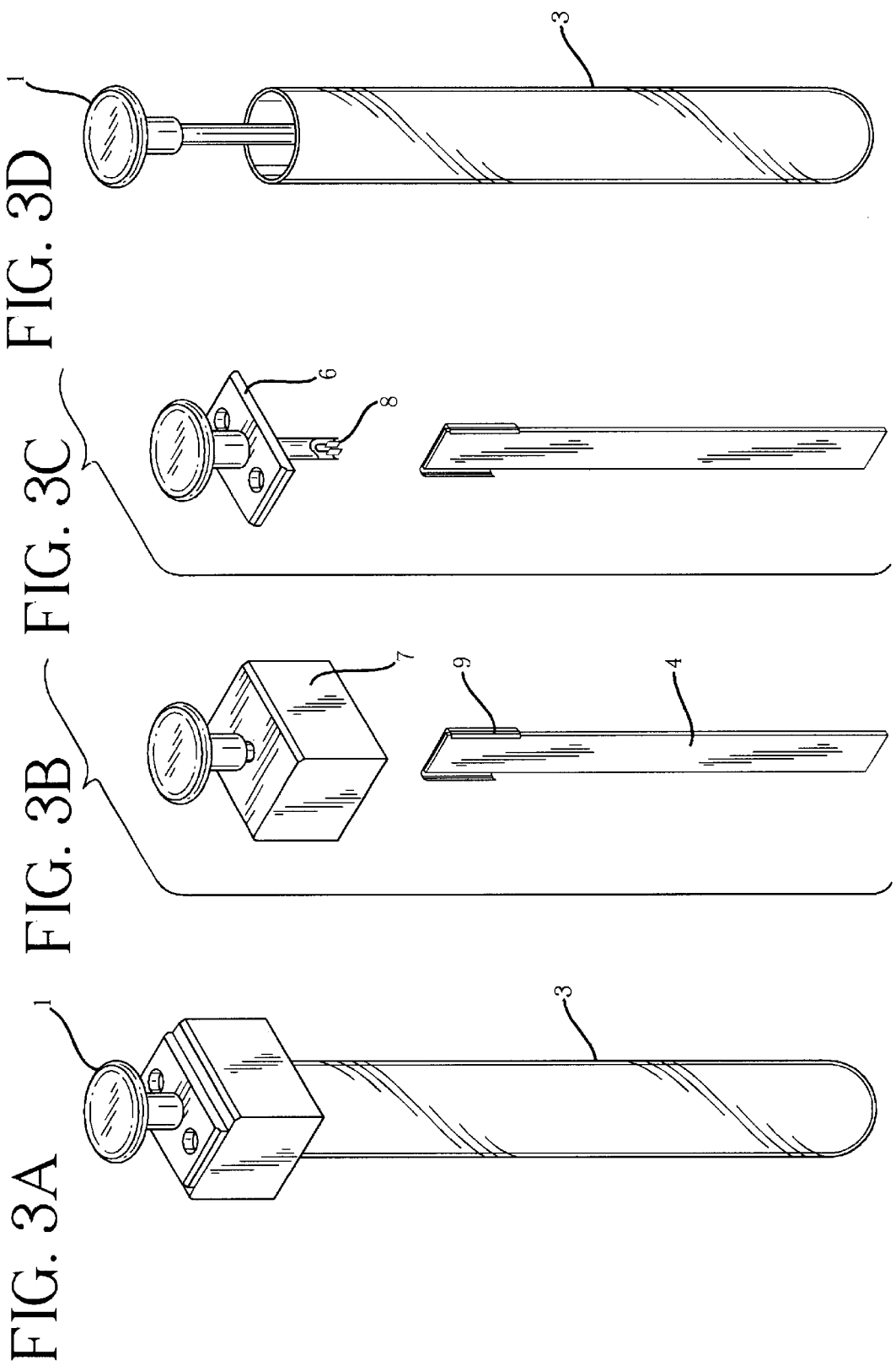
FIG. 3 is a series of exploded views of the invention.
Figure 7:
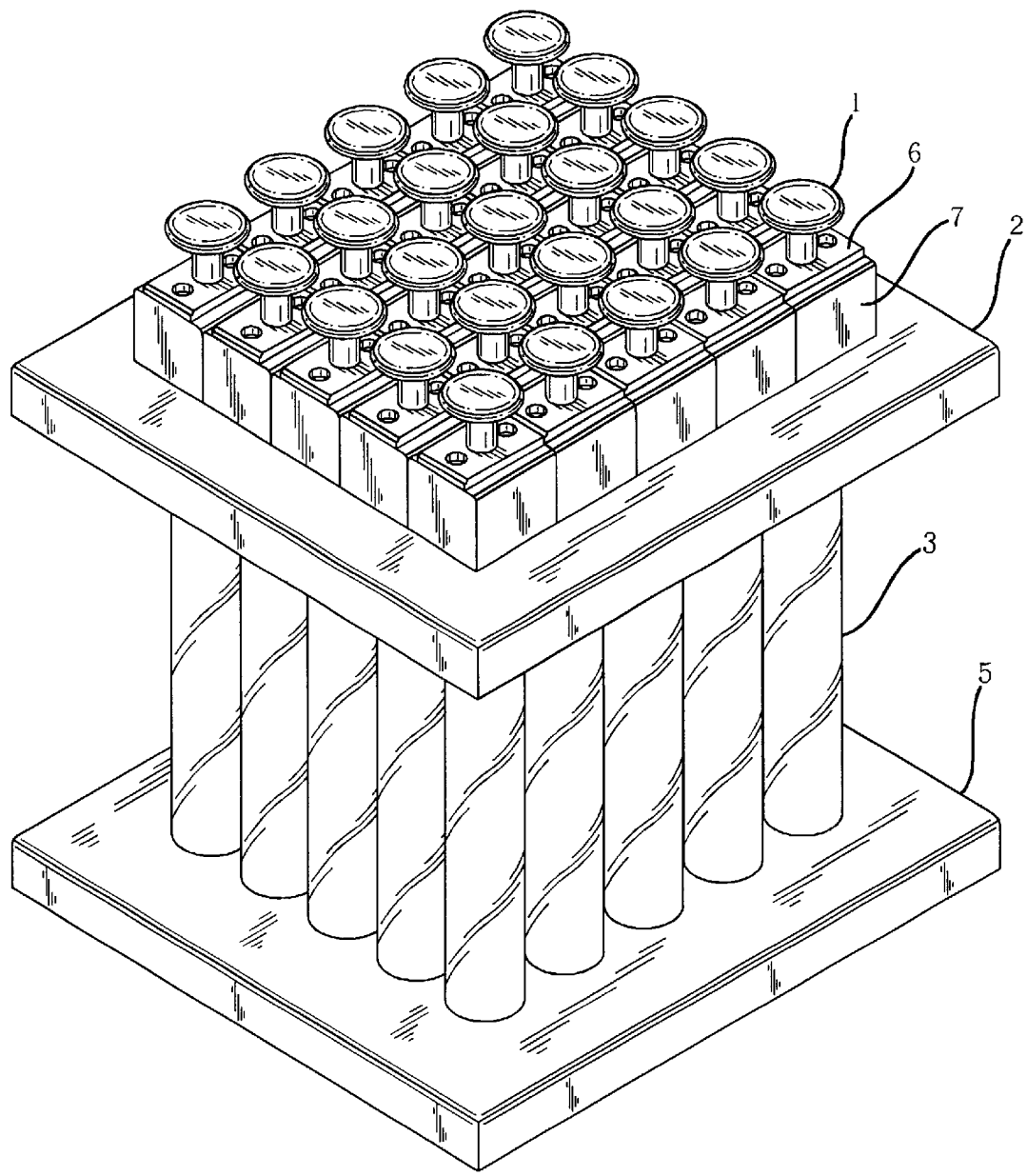
FIG. 7 is a perspective view of the invention with a five-by-five grid of TLC tubes.

The apparatus is constructed of a base 5 with cups (also referred to as receiving indentations herein) for holding the developing chambers 3. As shown in FIG. 1 and FIG. 7, the base 5 is connected to supports 10 for holding a top plate 2 which has holes for inserting and holding the developing chambers 3. A plunger 1 includes a manually accessible knob at an upper end and a shaft which extends through a plunger block 7 to enable a lower end of the plunger 1 to engage with the TLC plate 4 (see FIG. 3). Plunger block 7 rests on the top plate 2 and is coupled to the plunger 1 so that by lifting and lower the plunger 1, e.g., via the knob, the plunger block 7 (and the TLC plate 4) is also lifted and lowered. However, the plunger 1 can also be moved relative to the level of fluid in the chambers 3, i.e., slidable or movable within the plunger block 7. A mounting plate 6 holds the plunger block 7 and the plunger 1. The end of the plunger 1 is connected to a plate holding clip 8. The plate holding clip can be a compression fit, or a spring loaded clamp. An electrical alligator clip works adequately. The plate holding clip 8 is also attached to a plate holding frame 9 which fits over the edges of a TLC plate 4. The TLC plate 4 is suspended in the mobile phase at the bottom of the developing chamber 3. The plunger 1 may also allow the plate 4 to be raised or lowered relative to the solvent level.

Figure 4:
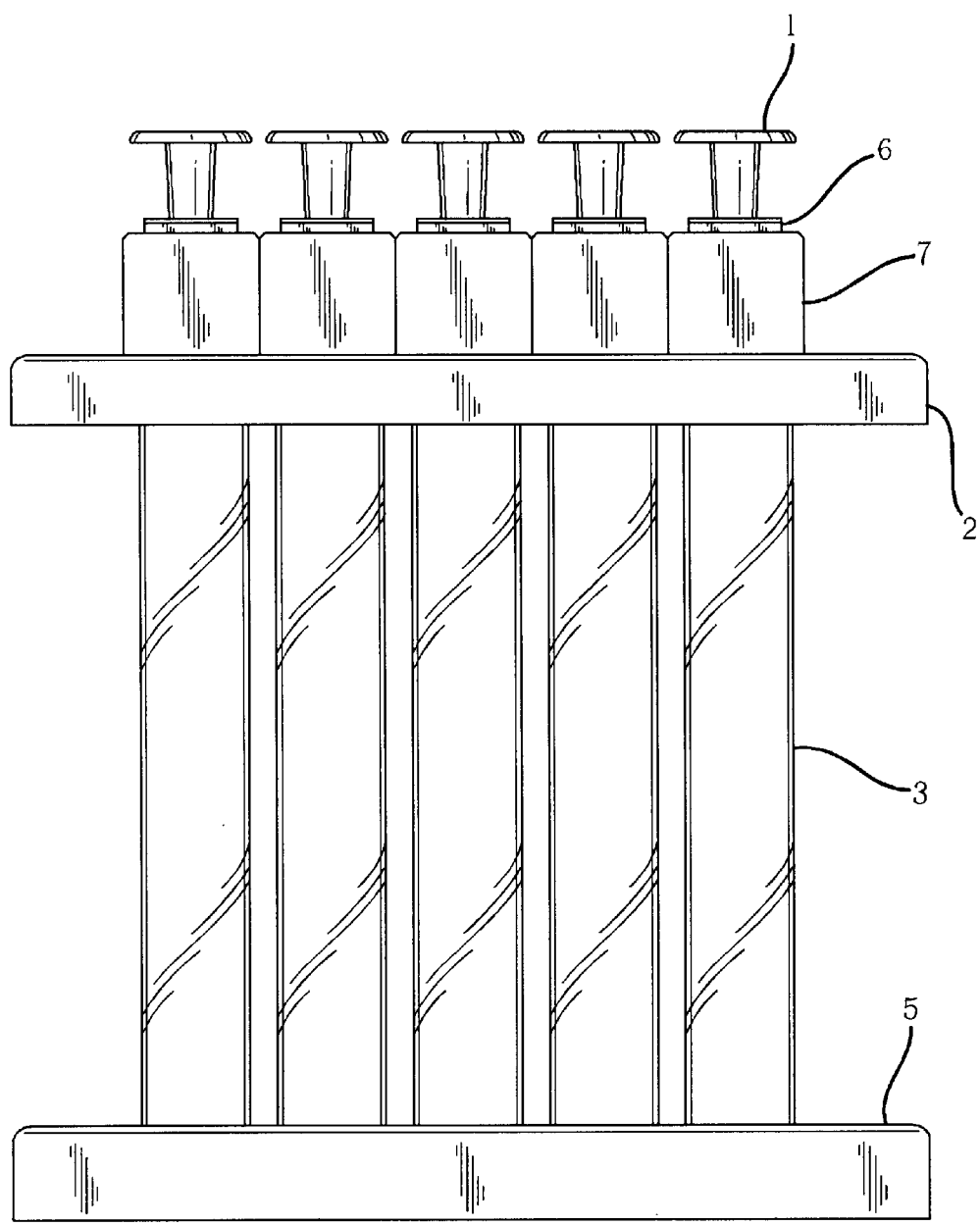
FIG. 4 is a side view of a five-wide grid of the invention.
Figure 5:
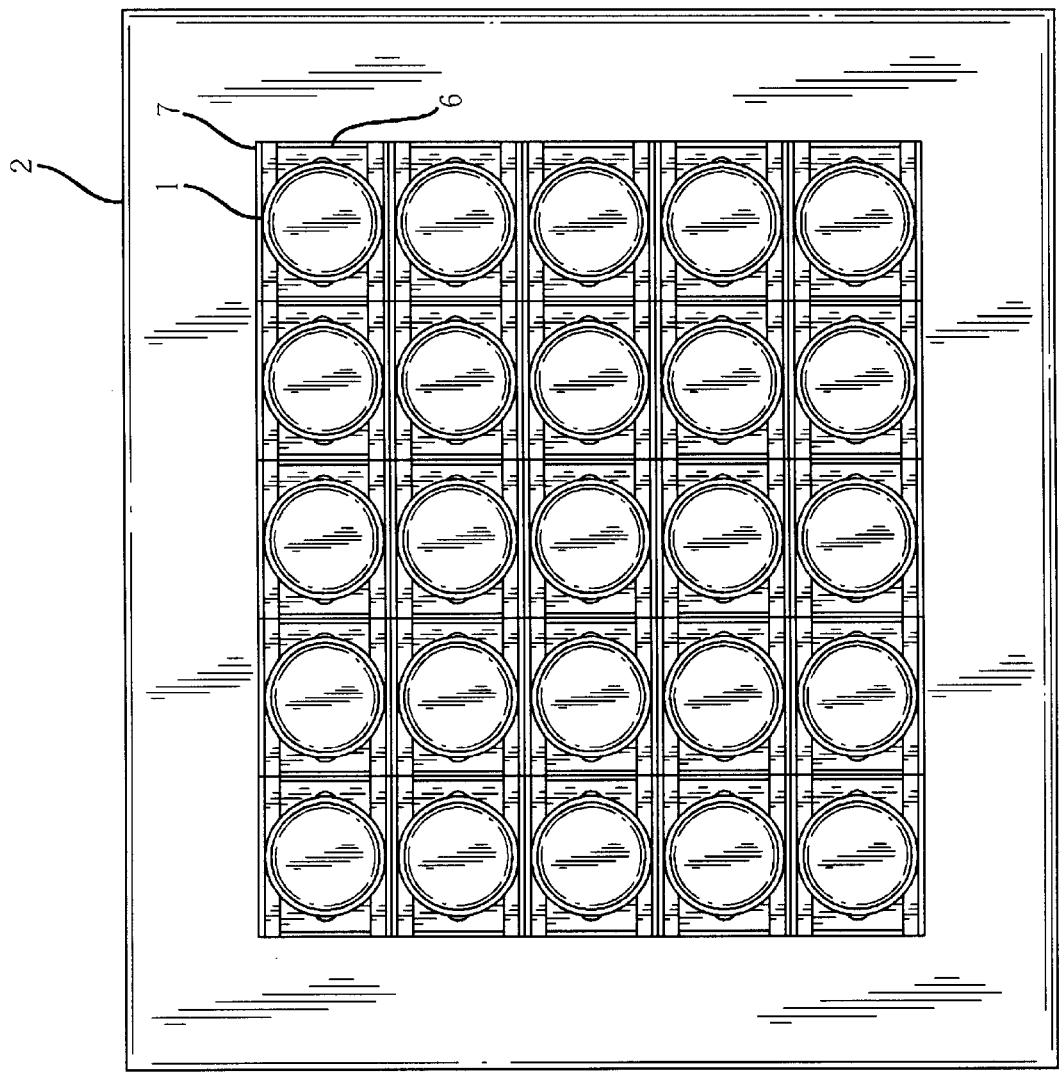
FIG. 5 is a top view of a five-by-five grid of the invention.
Figure 6:
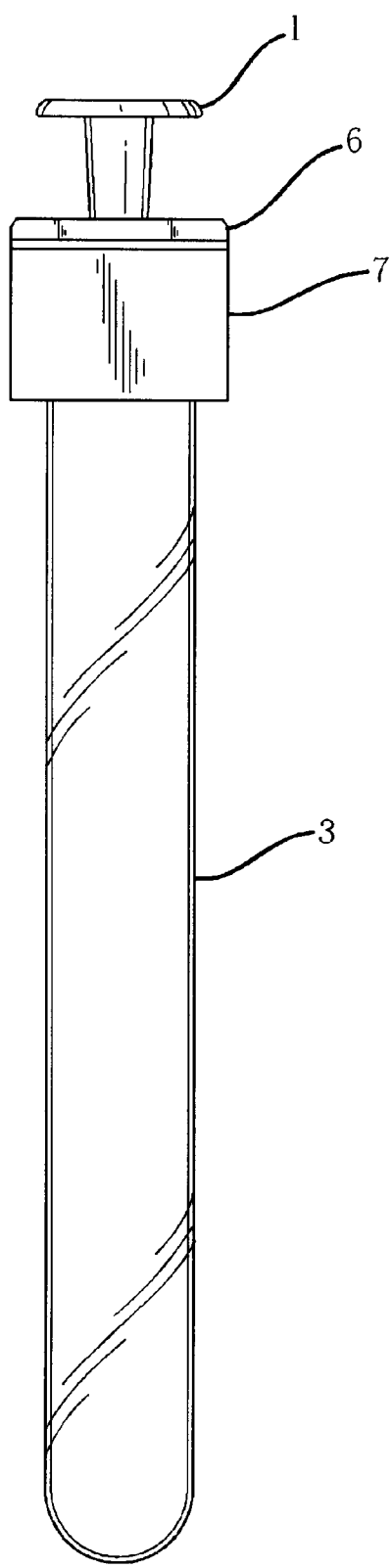
FIG. 6 is a side view of a single test tube with cap and plunger.

More particularly, it can be seen in FIG. 1 that there are five rows of plunger blocks 7 in the illustrated embodiment, each row being separate and uncoupled from the others. In use, each plunger block 7 has an associated plunger 1 and mounting plate 6 and is coupled to a plate holding clip 8, a plate holder frame 9 and a TLC plate 4. The demarcation between the rows of plunger blocks is shown most clearly in FIG. 4, a side view of the invention. Further as shown in FIGS. 1, 4 and 7, the top plate 2 and base plate 5 have substantially the same dimensions.

Using the apparatus of the invention allows the user to perform multiple tests simultaneously in a scientific manner. A 10×10 grid of developing chambers would allow rapid testing of 100 different tests of varying samples, adsorbents (stationary phases), and solvent combinations (mobile phases). The array of results will indicate the best way to proceed towards the purification of the sample, whether that be continued TLC testing to find proper conditions or the finding of proper conditions which can be transferred to column chromatography. Comparison of the number of spots, the Rf differences between spots, the shape of the spots, and the solubility of the simple in the prescribed mobile phase will aid in the evaluation.

Figure 2:
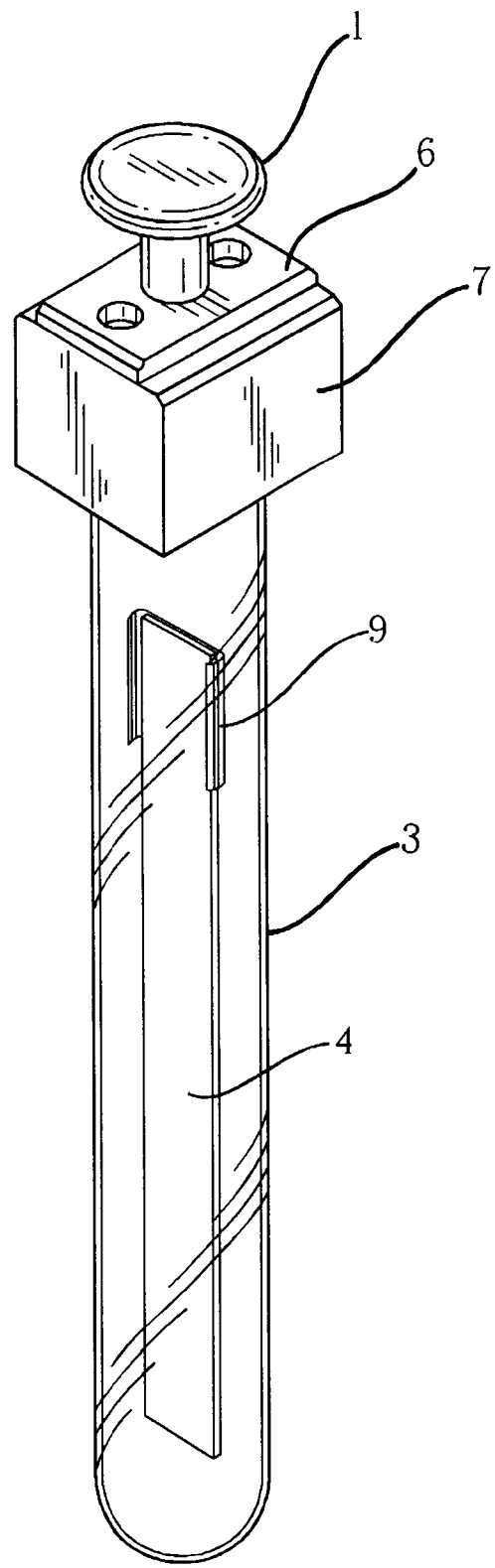
FIG. 2 is a drawing of a TLC developing chamber.

As shown in FIGS. 2, 3B and 3C, the plate holding frame 9 has a planar section and upturned edges whereby the TLC plate is positioned between the upturned edges.

What is claimed is:

1. An apparatus for conducting multiple thin layer chromatographic processes, comprising an array of receptacles, each of said receptacles being receivable of chromatographic fluid, said array comprising a plurality of parallel rows of receptacles, each of said rows including at least two of said receptacles adjacent one another, said receptacles in said rows being in respective alignment with one another such that a plurality of parallel columns of receptacles are present in said array, support means for supporting said receptacles, and retaining means coupled to said support means for retaining a plurality of thin layer chromatographic plates, said retaining means being structured and arranged to enable each of said plates to be inserted into and removed from a respective one of said receptacles.

2. The apparatus of claim 1, wherein said array comprises n×n receptacles.

3. The apparatus of claim 2, wherein n is an integer ranging from 5 to 10.

4. The apparatus of claim 1, wherein said support means comprise a top plate and a supporting base, said receptacles being at least partially situated between said top plate and said supporting base.

5. The apparatus of claim 4, wherein said top plate comprises a plurality of apertures, each of said receptacles being insertable into a respective one of said apertures.

6. The apparatus of claim 1, wherein said support means comprise a supporting base including a plurality of receiving indentations, each of said receptacles resting in a respective one of said indentations.

7. The apparatus of claim 1, wherein said retaining means comprise a plurality of plungers, each of said plungers being coupled to a respective one of said plates.

8. The apparatus of claim 7, wherein said retaining means further comprise plunger blocks, each of said plungers being coupled to one of said plunger blocks.

9. The apparatus of claim 8, wherein said support means comprise a top plate, said plunger blocks resting on said top plate to thereby support said plungers on said top plate.

10. The apparatus of claim 8, wherein said retaining means further comprise mounting plates arranged on said plunger blocks.

11. The apparatus of claim 8, wherein said plungers are movable within said plunger blocks to allow said plates to be raised or lowered relative to the level of chromatographic fluid in said receptacles.

12. The apparatus of claim 7, wherein said retaining means further comprise a plate holding frame interposed between each of said plungers and a respective one of said plates.

13. The apparatus of claim 12, wherein said plate holding frames have upturned edges whereby said plates are positioned between said upturned edges of said plate holding frames.

14. The apparatus of claim 12, wherein said retaining means further comprise plate holding clips each arranged to hold one of said plate holding frames and the respective one of said plates together by a compression fit.

15. The apparatus of claim 12, wherein said retaining means further comprise plate holding clips each arranged to hold one of said plate holding frames and the respective one of said plates together with a spring loaded clamp.

16. The apparatus of claim 15, wherein each of said plate holding clips is arranged at an end of a respective one of said plungers.

17. The apparatus of claim 14, wherein each of said plate holding clips is arranged at an end of a respective one of said plungers.

18. The apparatus of claim 1, wherein said retaining means are structured and arranged to retain each of said plates entirely in the respective one of said receptacles.

19. The apparatus of claim 1, wherein each of said receptacles is elongate and has a first closed end and a second open end, said retaining means being arranged to cover said second end of each of said receptacles such that each of said plates is situated in a respective one of said receptacles.

20. A thin layer chromatography assembly, comprising means fining a chamber having an open upper end and receivable of a chromatographic fluid, a plunger block for closing said upper end of said chamber, a movable plunger coupled to said plunger block, said plunger having an accessible portion exterior of said chamber and including a shaft extending through said plunger block, an end of said shaft being positionable in said chamber, a plate holding clip arranged at said end of said shaft, said end of said shaft being connected to said plate holding clip, and a thin layer chromatography plate retained by said plate holding clip.

21. The assembly of claim 20, further comprising a plate holding frame for retaining said plate, said plate holding clip being arranged to hold said plate holding frame and said plate together.

22. The assembly of claim 21, wherein said plate holding clip holds said plate holding frame and said plate together by a compression fit.

23. The assembly of claim 21, wherein said plate holding clip holds said plate holding frame and said plate together with a spring loaded clamp.

24. The assembly of claim 21, wherein said plate holding frame has opposed, upturned edges, said plate being retained between said upturned edges of said plate holding frame.

25. The assembly of claim 20, further comprising a mounting plate for holding said plunger block.

26. An apparatus for conducting multiple thin layer chromatographic processes, comprising an array of elongate receptacles, each of said receptacles having a closed first end and an open second end and being receivable of chromatographic fluid via said second end, support means for supporting said receptacles, and retaining means coupled to said support means for retaining a plurality of thin layer chromatographic plates, said retaining means being structured and arranged to enable each of said plates to be inserted into and removed from a respective one of said receptacles, said retaining means being arranged to cover said second end of each of said receptacles such that each of said plates is situated in a respective one of said receptacles.

27. A thin layer chromatography assembly, comprising means defining a chamber having an open upper end and receivable of a chromatographic fluid, a plunger block for closing said upper end of said chamber, a movable plunger coupled to said plunger block and having a first accessible end exterior of said chamber and a second end positionable in said chamber, a plate holding frame coupled to said second end of said plunger, said plate holding frame having opposed, upturned edges, and a thin layer chromatography plate retained between said upturned edges of said plate holding frame.

28. The assembly of claim 27, wherein said plunger includes a shaft extending through said plunger block and having an end positionable in said chamber, further comprising a plate holding clip arranged at said end of said shaft, said end of said shaft being connected to said plate holding clip, and said plate and said plate holding frame being held together by said plate holding clip.

* * * * *